(12) United States Patent
Mecikalski

(10) Patent No.: US 7,802,570 B2
(45) Date of Patent: Sep. 28, 2010

(54) DRUG TRANSFER DEVICE

(75) Inventor: Mark B. Mecikalski, Tucson, AZ (US)

(73) Assignee: Breathe Pharmaceuticals, San Diego, CA (US)

( * ) Notice: Subject to any disclaimer, the term of this patent is extended or adjusted under 35 U.S.C. 154(b) by 0 days.

(21) Appl. No.: 11/965,662

(22) Filed: Dec. 27, 2007

(65) Prior Publication Data

US 2008/0173302 A1 Jul. 24, 2008

Related U.S. Application Data

(60) Provisional application No. 60/886,476, filed on Jan. 24, 2007.

(51) Int. Cl.
*A61M 15/00* (2006.01)
*A61M 16/00* (2006.01)

(52) U.S. Cl. .................... 128/203.21; 128/203.12; 128/203.15; 128/203.19; 128/203.23; 128/203.24; 604/58; 222/636

(58) Field of Classification Search ............ 128/203.21, 128/203.12, 203.15, 203.13, 203.19, 203.24, 128/204.11, 204.13, 204.14; 604/58; 222/636
See application file for complete search history.

(56) References Cited

U.S. PATENT DOCUMENTS

| 4,069,819 | A | * | 1/1978 | Valentini et al. | ....... | 128/203.15 |
|---|---|---|---|---|---|---|
| 5,042,472 | A | | 8/1991 | Bunin | | |
| 5,152,284 | A | | 10/1992 | Valentini et al. | | |
| 5,239,991 | A | * | 8/1993 | Chawla et al. | ......... | 128/203.15 |
| 5,301,666 | A | * | 4/1994 | Lerk et al. | ............ | 128/203.15 |
| 5,469,843 | A | | 11/1995 | Hodson | | |
| 5,483,954 | A | * | 1/1996 | Mecikalski | ............ | 128/203.15 |
| 5,533,502 | A | | 7/1996 | Piper | | |
| 5,560,490 | A | | 10/1996 | Chawla | | |
| 5,568,807 | A | * | 10/1996 | Mecikalski | ............ | 128/203.21 |
| 5,575,281 | A | * | 11/1996 | Mecikalski | ............ | 128/203.21 |
| 5,622,166 | A | * | 4/1997 | Eisele et al. | ........... | 128/203.15 |
| 5,669,378 | A | | 9/1997 | Pera et al. | | |
| 5,727,546 | A | | 3/1998 | Clarke et al. | | |
| 5,740,794 | A | * | 4/1998 | Smith et al. | ............ | 128/203.15 |

(Continued)

FOREIGN PATENT DOCUMENTS

WO 2008/091355 7/2008

OTHER PUBLICATIONS

Mecikalski; "Improving DPI Performance by using inspiratory pressure threshold drug release and inspiratory flow control" *Respiratory Drug Delivery VI Hilton Head, South Carolina*, May 3-7, 1998, pp. 373-375.

*Primary Examiner*—Tatyana Zalukaeva
*Assistant Examiner*—Clinton Ostrup
(74) *Attorney, Agent, or Firm*—Fred C. Hernandez; Mintz, Levin, Cohn, Ferris, Glovsky and Popeo, P.C.

(57) ABSTRACT

A drug transfer system is adapted to transfer a powdered drug into a patient via inhalation. The drug transfer system includes a drug container or packet that removably inserts into an inhaler device. As the patient inhales from the inhaler device, the drug flows from the container, through the inhaler device, and into the patient's respiratory system. The system is adapted for ease of use without requiring the user to perform any cumbersome manipulations of the drug packet during insertion into the inhaler or during inhalation of the drug.

26 Claims, 12 Drawing Sheets

U.S. PATENT DOCUMENTS

| | | | |
|---|---|---|---|
| 5,787,881 A | 8/1998 | Chawla | |
| 5,918,594 A | 7/1999 | Asking et al. | |
| 6,029,663 A * | 2/2000 | Eisele et al. | 128/203.21 |
| 6,082,356 A * | 7/2000 | Stradella | 128/203.15 |
| 6,089,228 A * | 7/2000 | Smith et al. | 128/203.15 |
| 6,098,619 A | 8/2000 | Britto et al. | |
| 6,102,035 A | 8/2000 | Asking et al. | |
| 6,109,261 A | 8/2000 | Clarke et al. | |
| D441,859 S | 5/2001 | Pera | |
| 6,240,918 B1 | 6/2001 | Ambrosio et al. | |
| 6,257,233 B1 * | 7/2001 | Burr et al. | 128/203.21 |
| 6,286,507 B1 | 9/2001 | Jahnsson | |
| 6,428,769 B1 | 8/2002 | Rubsamen et al. | |
| 6,484,717 B1 | 11/2002 | Dagsland et al. | |
| 6,520,179 B1 | 2/2003 | Von Schuckmann et al. | |
| 6,579,968 B1 | 6/2003 | Blood et al. | |
| 6,626,173 B2 | 9/2003 | Genova et al. | |
| 6,732,943 B2 * | 5/2004 | Srinivasan | 239/1 |
| 6,794,489 B2 | 9/2004 | Blood et al. | |
| 6,832,419 B1 | 12/2004 | Williamson et al. | |
| 6,915,802 B1 | 7/2005 | Anderson et al. | |
| 6,923,175 B2 | 8/2005 | Poole et al. | |
| 6,941,947 B2 * | 9/2005 | Young et al. | 128/203.21 |
| 6,998,496 B2 | 2/2006 | Luchini et al. | |
| 7,025,056 B2 | 4/2006 | Eason et al. | |
| 7,025,057 B2 | 4/2006 | Chawla | |
| 7,080,644 B2 * | 7/2006 | Gumaste | 128/203.21 |
| 2002/0078947 A1 * | 6/2002 | Gumaste | 128/203.21 |
| 2003/0025008 A1 * | 2/2003 | Srinivasan | 239/589 |
| 2007/0235029 A1 * | 10/2007 | Zhu et al. | 128/203.15 |

* cited by examiner

DRUG TRANSFER DEVICE

REFERENCE TO PRIORITY DOCUMENT

This application claims priority of U.S. Provisional Patent Application Ser. No. 60/886,476 filed Jan. 24, 2007. Priority of the aforementioned filing date is hereby claimed and the disclosure of the Provisional Patent Application is hereby incorporated by reference in its entirety.

BACKGROUND

The present disclosure relates to systems and methods for oral inhalation of drugs or other medications.

Some respiratory diseases respond to treatment via direct application of a drug. Such drugs are typically in a powdered format such that the delivery of the drug into the patient is achieved by inhaling the drug via the patient's mouth. As a result, the drug is deposited directly into the patient's respiratory system which can maximize the utilization of the drug. The powdered drug can also be used for treatment of diseases other than those of the respiratory system. The drug is deposited on the very large surface areas of the respiratory tract so that the drug is rapidly absorbed into the blood stream. The application of the drug via inhalation can advantageously replace drug of administration by injection, tablet, or other means.

A handheld inhalation device is typically used to transfer the drug from a drug container, such as a packet, into the patient's respiratory system. The device usually includes a mouthpiece that inserts into the patient's mouth. The patient inserts the drug container into the device and then inhales from the mouthpiece to initiate airflow into the drug container and into the device. The airflow sweeps the drug out of the container, into the device, and into the patient's mouth where the drug passes into the patient's respiratory system.

Current drug inhalation devices can be cumbersome and difficult to use. Thus, there is a need for improved devices and methods for transferring a drug to a patient via the patient's respiration.

SUMMARY

A drug transfer system is adapted to transfer a powdered drug into a patient via inhalation. The drug transfer system includes a drug container or packet that removably inserts into an inhaler device. As the patient inhales from the inhaler device, the drug flows from the container, through the inhaler device, and into the patient's respiratory system. The drug packet includes features that facilitate monitoring of drug dosage during inhalation such as a transparent blister that provides a visual indication of the drug inside the packet. In addition, the drug packet docks into the inhaler in a quick and easy fashion that increases the likelihood that a proper drug dosage will be inhaled during use. The system is adapted for ease of use without requiring the user to perform any cumbersome manipulations of the drug packet during insertion into the inhaler or during inhalation of the drug.

Other features and advantages should be apparent from the following description of various embodiments, which illustrate, by way of example, the principles of the invention.

DETAILED DESCRIPTION

A drug transfer system is adapted to transfer a powdered drug into a patient via inhalation. The drug transfer system includes a drug container or packet that removably inserts into an inhaler device. As the patient inhales from the inhaler device, the drug flows from the container, through the inhaler device, and into the patient's respiratory system. The drug packet includes features that facilitate monitoring of drug dosage during inhalation such as a transparent blister that provides a visual indication of the drug inside the packet. In addition, the drug packet docks into the inhaler in a quick and easy fashion that increases the likelihood that a proper drug dosage will be inhaled during use. The system is adapted for ease of use without requiring the user to perform any cumbersome manipulations of the drug packet during insertion into the inhaler or during inhalation of the drug.

Figure 1:
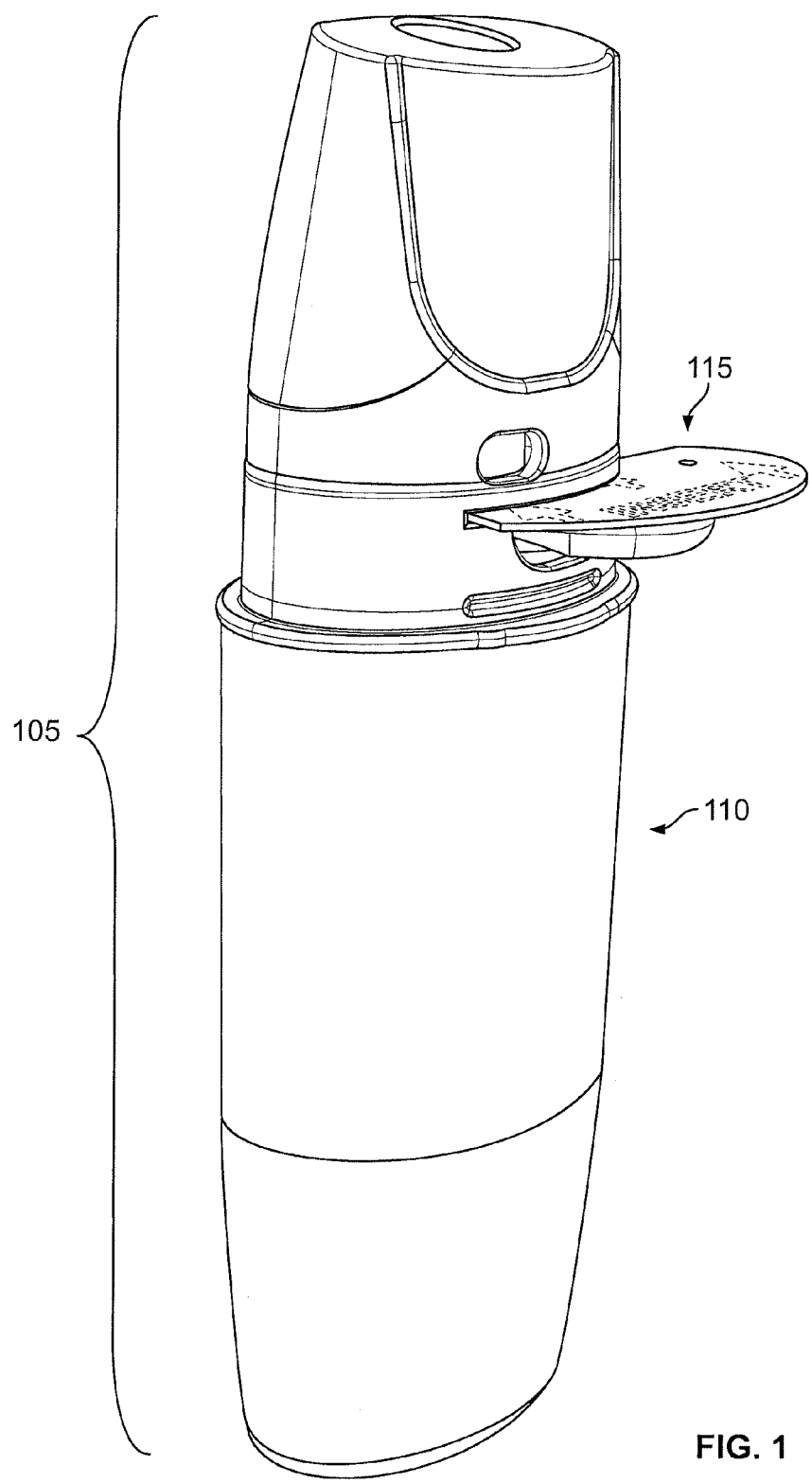
FIGS. 1 and 2 show perspective view of a drug transfer system that is adapted to transfer a drug into a user via inhalation.
Figure 2:
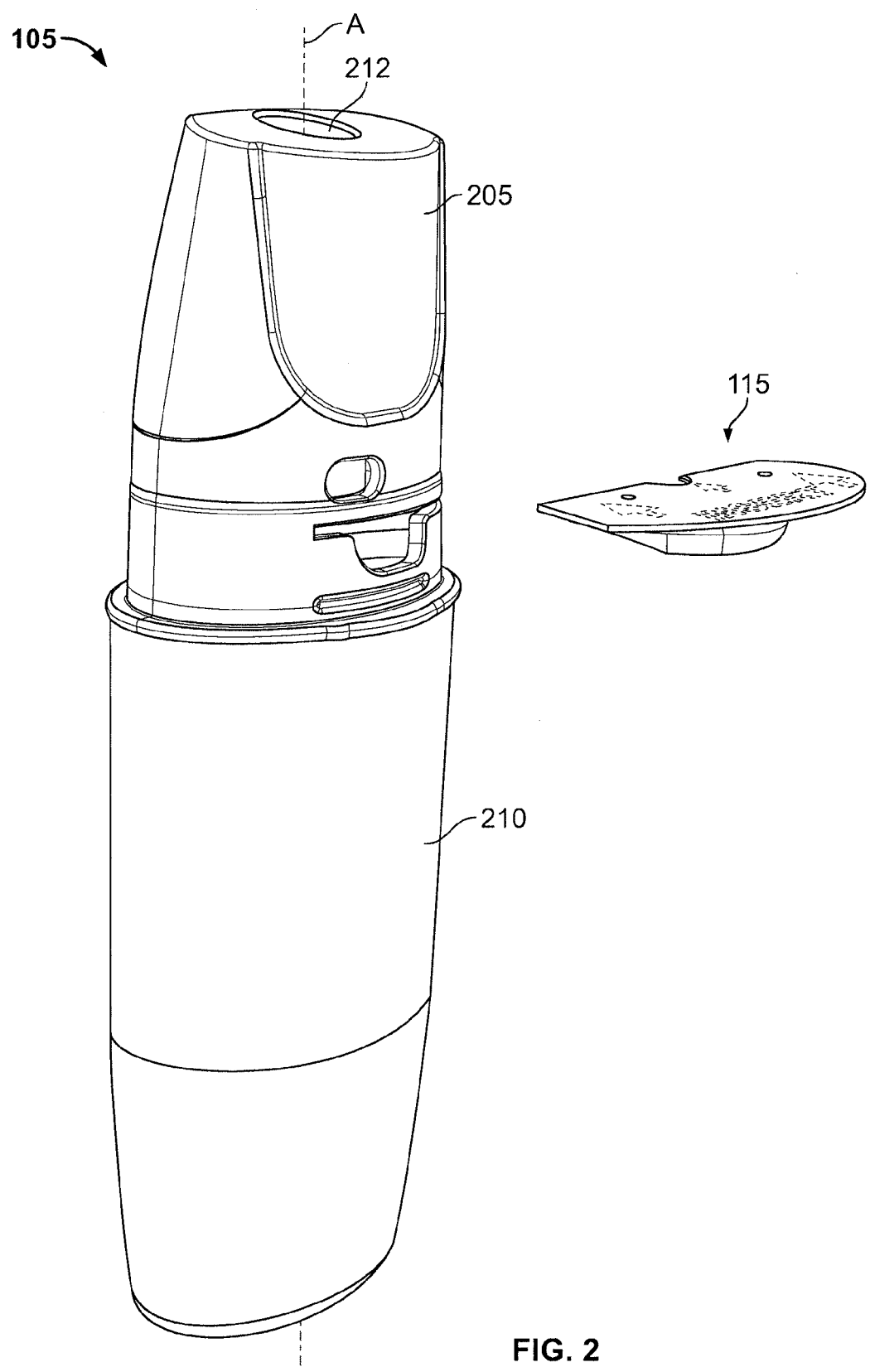

FIGS. 1 and 2 show perspective view of a drug transfer system 105 that is adapted to transfer at least one drug into a user, such as a patient, via inhalation. The drug transfer system 105 includes an inhaler 110 and a drug container 115. The inhaler 110 is adapted to at least partially be inserted into a mouth of the patient for transferring drug from the drug container 115 into the patient's mouth in response to the patient inhaling from the inhaler 110. In this regard, the drug container 115 contains a drug substance such as in a powdered form. The drug container 115 can be removably inserted or docked into the inhaler 110 (as shown in FIG. 1) during use and removed from the container 115 (as shown in FIG. 2) after use.

With reference to FIG. 2, the inhaler 110 has a structure that is sized and shaped for at least partial insertion in the patient's mouth. In an embodiment, the inhaler 110 has an elongated shape that extends generally along an axis A, although it should be appreciated that the inhaler 110 can have various other shapes. The inhaler 110 includes a mouthpiece 205 that inserts into the patient's mouth. The mouthpiece 205 is removably coupled to a cap 210 which can be adapted to provide storage space for one or more drug containers. When the mouthpiece 205 is inserted into the patient's mouth, the patient can inhale from an airflow port 212 in the mouthpiece to cause air to flow into the mouthpiece via an opening 425. During inhalation, the air interacts with the drug container 115 to disaggregate the contained drug such that the drug flows out of the mouthpiece 205 and into the patient's mouth, as described below.

Figure 3:
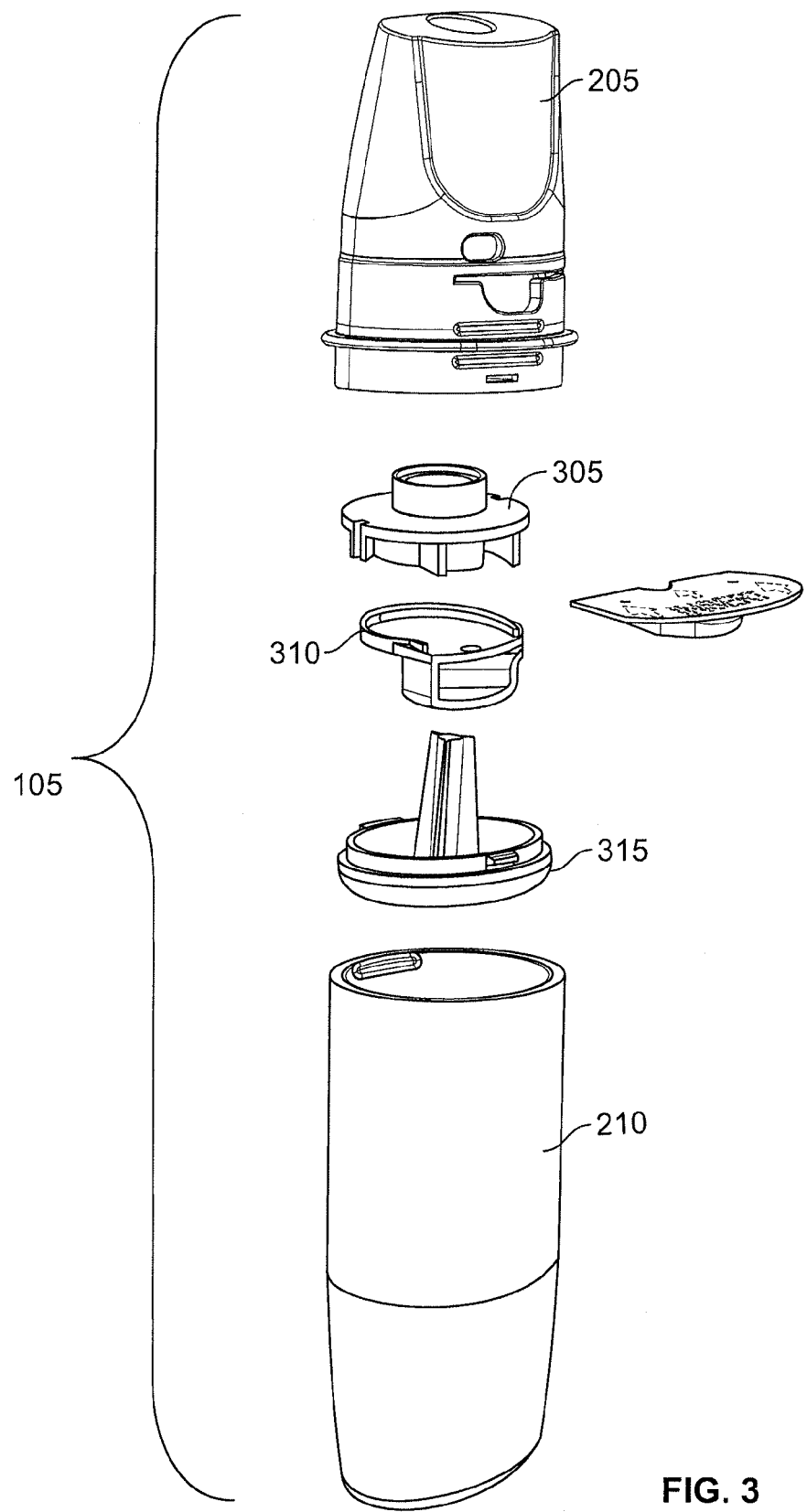
FIG. 3 shows an exploded view of the drug transfer system.

The mouthpiece 205 contains one or more internal members that facilitate airflow through the inhaler 110 in a manner that disaggregates the drug during the patient's inhalation. For example, the mouthpiece 205 can contain one or more internal structures as shown in the exploded view of the inhaler 110 of FIG. 3. In an embodiment, the internal structures include an airflow guide 305, a drug container interface 310, and a lower base 315. The airflow guide 305 is adapted to guide air such that the air flows through the inhaler 110 in a predetermined manner during the patient's inhalation. The drug container interface 310 is adapted to receive the drug container 115 in a manner that positions the drug container 115 in a proper orientation for use. The lower base 315 mounts to the bottom of the mouthpiece 205 for securing the airflow guide 305 and drug container interface 310 therein. The airflow guide 305 and drug container interface 310 are described in more detail below. It should be appreciated that the structure of the internal components shown in FIG. 3 is exemplary and can be varied. For example, the individual components can be combined into a single component or can be integrated as a single or multiple components with the mouthpiece 205.

Figure 4A:
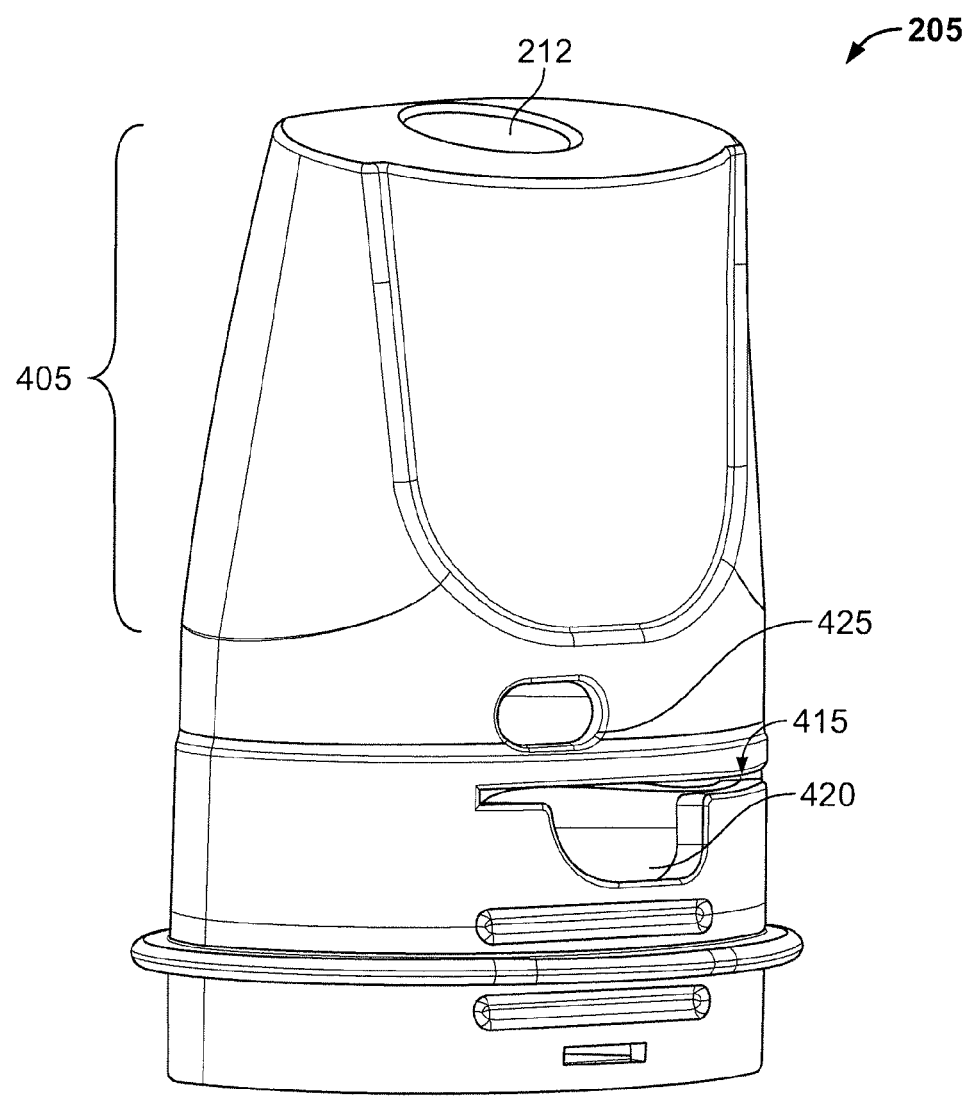
FIGS. 4A and 4B show perspective views of a mouthpiece of the system.
Figure 4B:
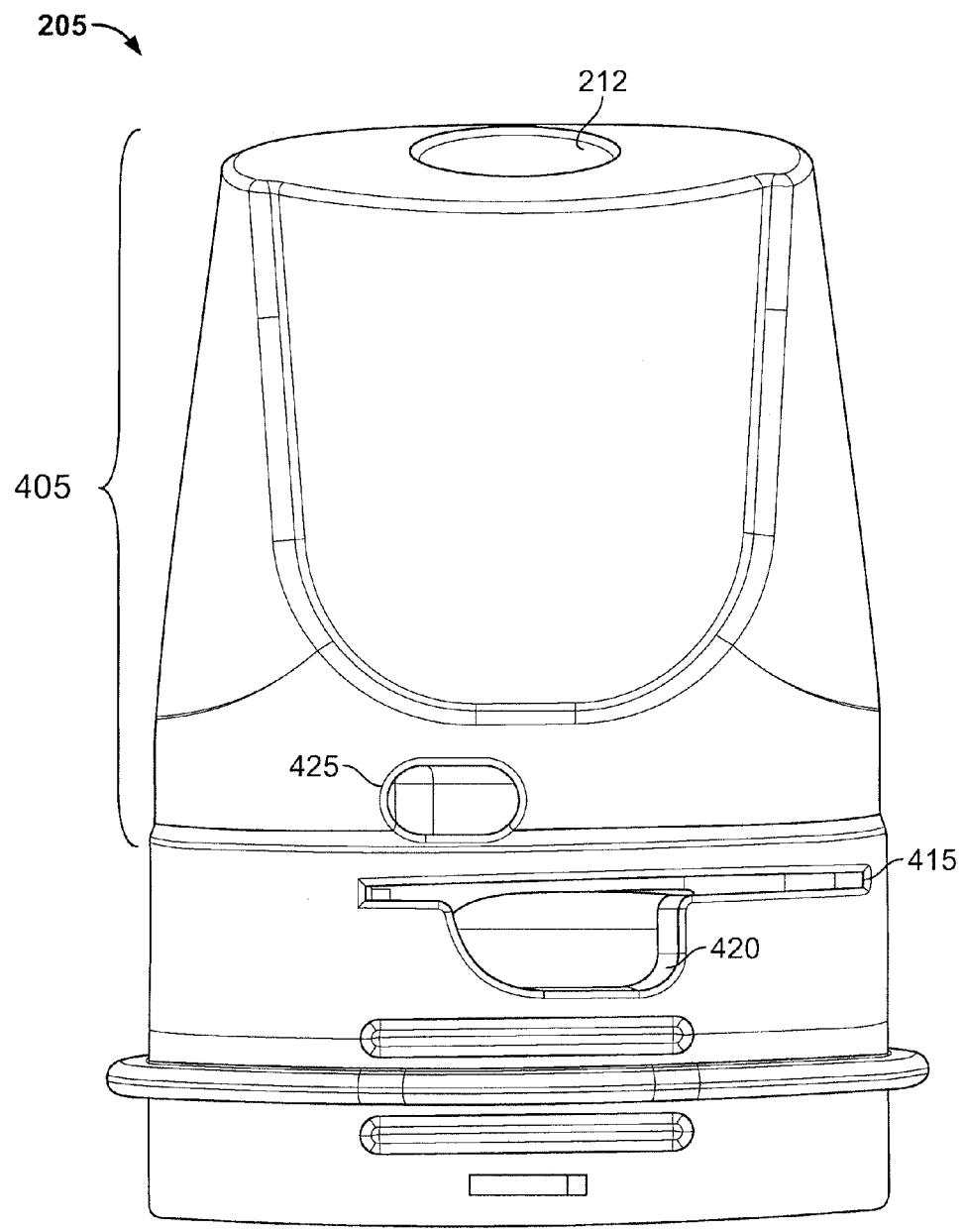

FIGS. 4A and 4B show perspective views of the mouthpiece 205. The mouthpiece 205 can have any of a variety of shapes adapted to fit at least partially within the mouth of a patient. In an embodiment, the mouthpiece 205 is shaped to facilitate a comfortable insertion into the patient's mouth and to facilitate the patient pursing his or her lips around the mouthpiece 205 during inhalation. For example, the mouthpiece 205 can include an insertion region 405 that is sized and shaped for insertion into the patient's mouth. The insertion region 405 tapers from a first size to a smaller size to provide the mouthpiece 205 with a sloped contour. As mentioned, an airflow port 212 extends through one end of the insertion region 405. The airflow port 212 communicates with an internal flow chamber 605 (FIG. 6) within the mouthpiece 205.

With reference still to FIGS. 4A and 4B, the mouthpiece 205 includes an interface 415 that is adapted to receive the drug container 115 (as shown in FIG. 1). In an embodiment, the interface 415 is an opening that is sized and shaped to receive the drug container 115. For example, the interface 415 can be an elongated slot that has a width and length that compliments the width and length of at least a portion of the drug container 115. The slot communicates with the internal drug container interface 310 (FIG. 3) located inside the mouthpiece 205. In the illustrated embodiment, the interface 415 has an enlarged region 420 that facilitates insertion and removal of the drug container 115 into and out of the interface 420.

The mouthpiece includes an airflow opening 425 that communicates with the airflow port 212 via the internal airflow guide 305 (FIG. 3) inside the mouthpiece 205. The airflow opening 425 is positioned immediately above the interface 415 in the embodiment of FIGS. 4A and 4B, although the airflow opening 425 can be positioned in other locations. For example, in order to protect airflow opening 425 from being occluded by the patient's fingers during operation, it may be located to the right of aperture 420 and inferior to slot 415, where it is protected from finger or thumb occlusion by the inserted drug container 115. When the patient inhales through the airflow port 212 in mouthpiece 205, air flows into the mouthpiece 205 through the airflow opening 425. The air then flows through the airflow guide 305 and out of the airflow port 212 into the patient's mouth. During this process, some additional air passes through the drug container 115 and sweeps drug from the container into the inhaler, and thence into patient's mouth, as described in further detail below.

Figure 5:
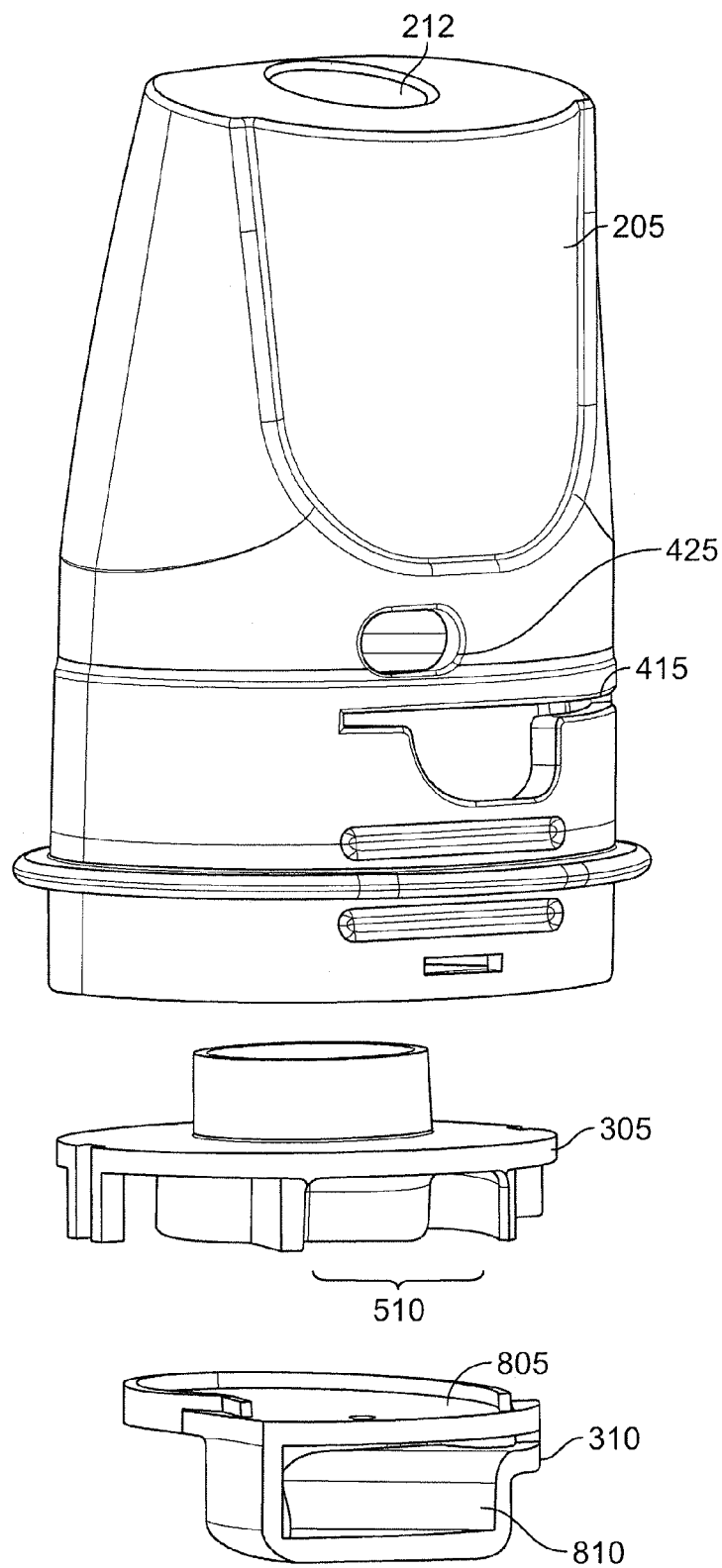
FIGS. 5 and 6 show perspective, exploded views of the mouthpiece and internal components
Figure 6:
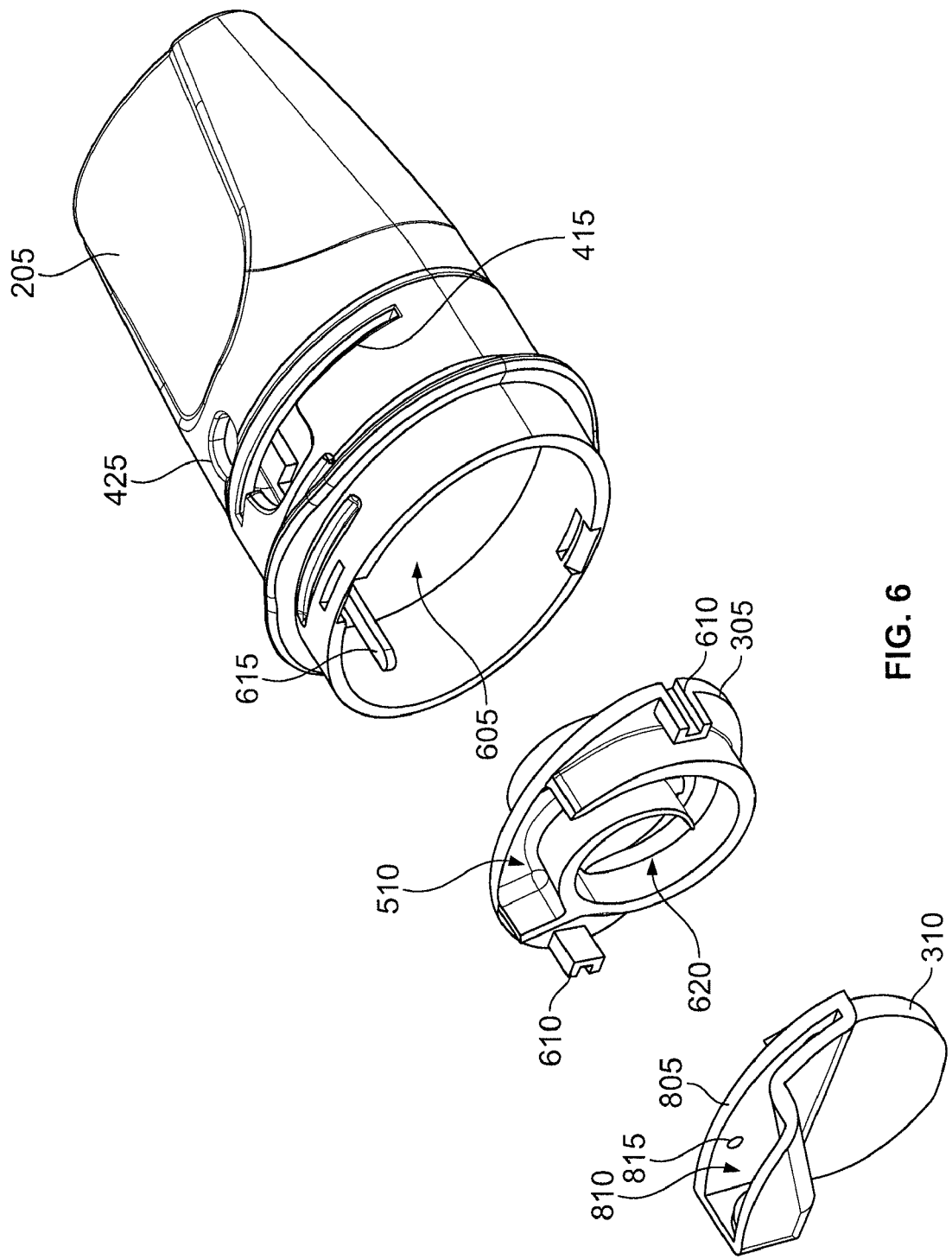

FIGS. 5 and 6 show perspective, exploded views of the mouthpiece 205 and internal components. As shown in FIG. 6, the mouthpiece 205 has an internal chamber 605 through which air flows during the patient's inhalation from the mouthpiece 205. The internal chamber 605 provides a space for housing the airflow guide 305 and the drug container interface 310 in the assembled device. Internal chamber 605 may contain additional airflow components to guide the aerosol stream to the oral exit 212. In this regard, the airflow guide 305 has one or more guide members 610, such as slots, that couple to complimentary guide members 615, such as ribs, in the mouthpiece 205 for coupling the airflow guide 305 into the mouthpiece. It should be appreciated that other structures can be used to couple the internal components into the mouthpiece.

With reference to FIGS. 5 and 6, the airflow guide 305 has a mouth or entryway 510 through which air enters into the airflow guide 305 during patient inhalation. The entryway 510 communicates with the airflow opening 425 in the mouthpiece 205 when the mouthpiece is fully assembled. The entryway 510 of the airflow guide 305 leads into a disaggregation chamber 620 through which air flows during patient inhalation. The disaggregation chamber 620 can have various configurations. In one embodiment, the disaggregation chamber 620 is spiral in shape such that air flows from the entryway 510 along a spiral pathway.

Figure 7:
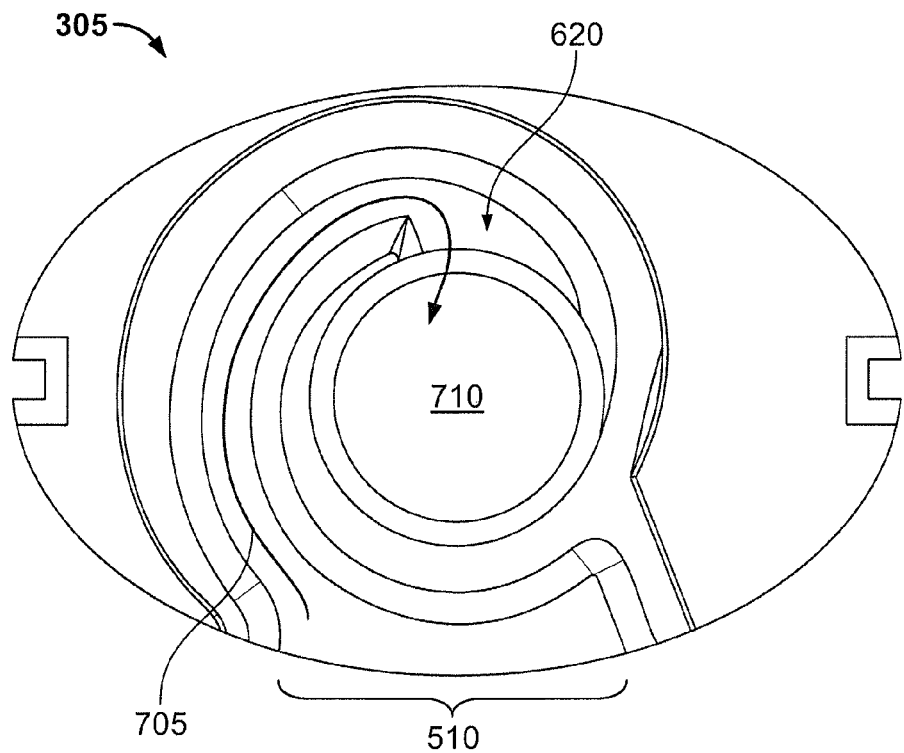
FIG. 7 shows a bottom view of a airflow guide component of the mouthpiece.

FIG. 7 shows a bottom view of the airflow guide 305. The disaggregation chamber 620 defines a helical or spiral pathway 705 that begins at the entryway 510 and leads to aperture that forms an exit way 710 that communicates with the internal chamber 605 of the mouthpiece 205. The exit way 710 is located in a central position of the airflow guide 305 below the airflow port 212 of the mouthpiece 205. The spiral pathway can vary in length and can include various quantity of cyclical movements along its length. The length of the pathway can be decreased or increased to increase the number of spirals and can also include more than one levels along three dimensions in case more space for disaggregation is needed. Moreover, although the disaggregation chamber 620 defines a spiral pathway in the illustrated embodiment, it should be appreciated that the pathway need not be spiral.

Figure 8:
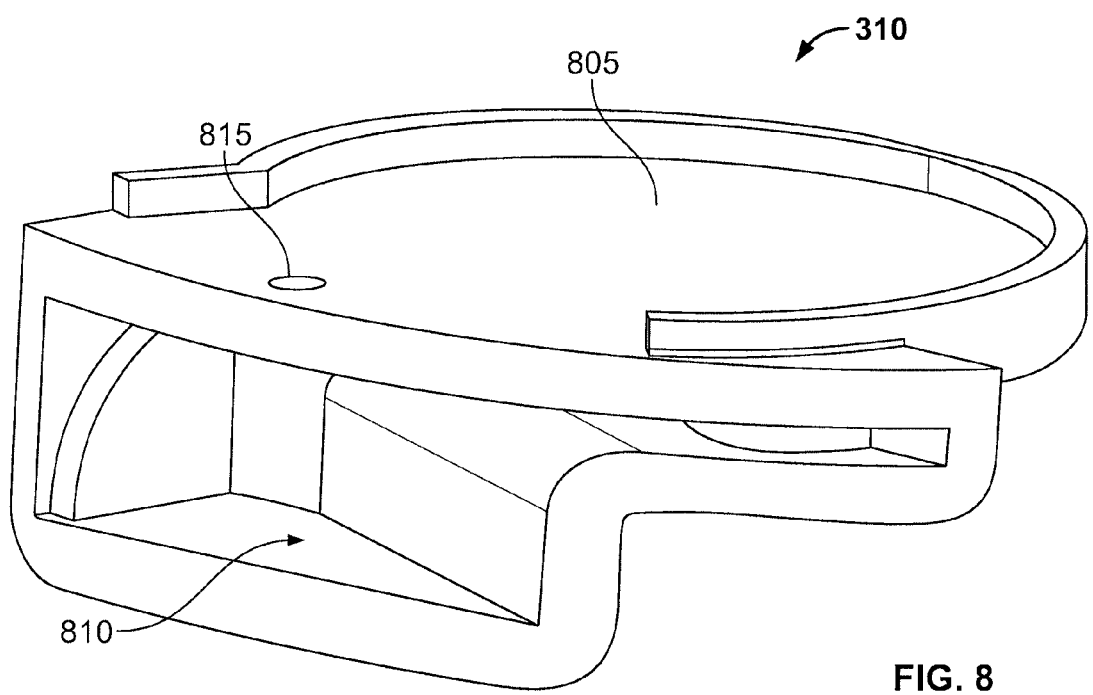
FIG. 8 shows a perspective view of a container interface of the mouthpiece.

With reference again to FIGS. 5 and 6, the container interface 310 is disposed beneath the airflow guide 305. FIG. 8 shows a perspective view of the container interface 310. With reference to FIGS. 5, 6, and 8, the container interface 310 has an upper wall 805 that abuts the lower edge of the airflow guide 305 to enclose the disaggregation chamber 620 in the assembled device. In addition, the container interface 310 includes a receptacle 810 comprised of an opening sized and shaped to compliment the size and shape of the interface 415 of the mouthpiece 205. The receptacle 810 aligns with the interface 415 on the mouthpiece 205 when the device is assembled. In this manner, the drug container 115 inserts into the receptacle 810 when the drug container 115 is inserted through the interface 415 in the mouthpiece 205. The receptacle 810 is sized and shaped to guide the drug container into a proper position relative to the inhaler during insertion of the drug container into the inhaler, a described in further detail below.

With reference to FIG. 8, the container interface 310 includes an airflow port 815 formed of a hole that extends through the upper wall 805 such that the airflow port 815 communicates with the receptacle 810. The airflow port 815 aligns with and communicates with at least a portion of the disaggregation chamber 620 of the airflow guide 305 when the device is assembled. In this manner, air can flow through the airflow port 815 into the disaggregation chamber 620 upon inhalation of the patient. In addition, when the drug container 115 is docked into the inhaler, the airflow port 815 communicates with a corresponding port in the drug container 115 as described in further detail below.

The inhaler 110 can be manufactured of any of a variety of materials including, for example, food grade moldable plastics, such as polyethylene, polypropylene, ABS, or the like.

Figure 9:
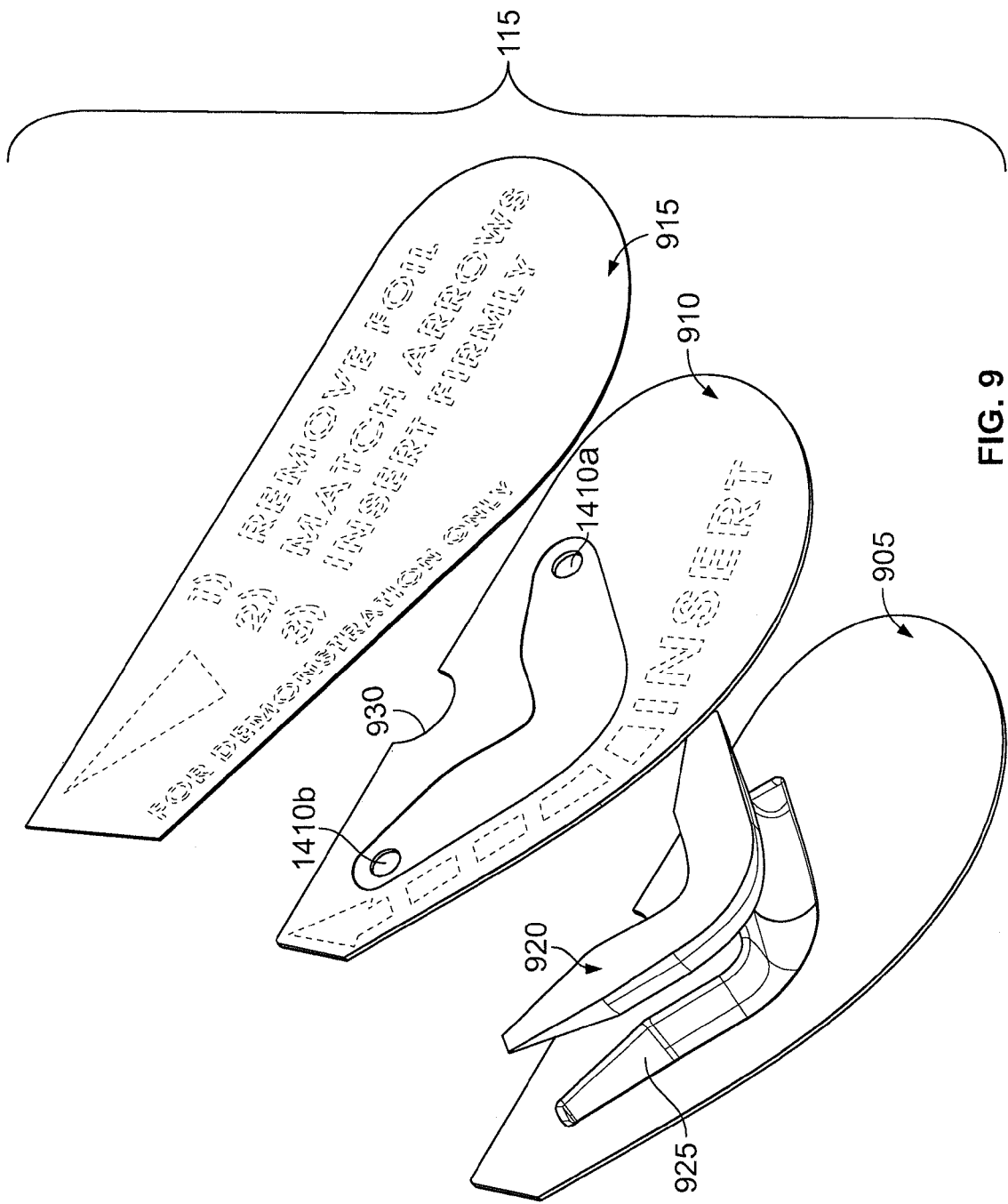
FIG. 9 shows an exploded, perspective view of a drug container of the drug transfer system.

FIG. 9 shows an exploded, perspective view of the drug container 115. In an embodiment, the drug container 115 generally includes a blister member 905, a blister lid 910 attached to the blister member 905, and a removable lid 915 attached to the blister lid 910. The blister member 905 and the blister lid 910 collectively enclose and contain a drug 920 within a drug chamber 925. The drug 920 is schematically represented in FIG. 9 as a solid piece of material having a shape that conforms to the shape of the chamber 925. However, the drug 920 can be in a powdered format such that the drug 920 is formed of a plurality of granules or particles that are housed within the drug chamber 925.

Figure 10:
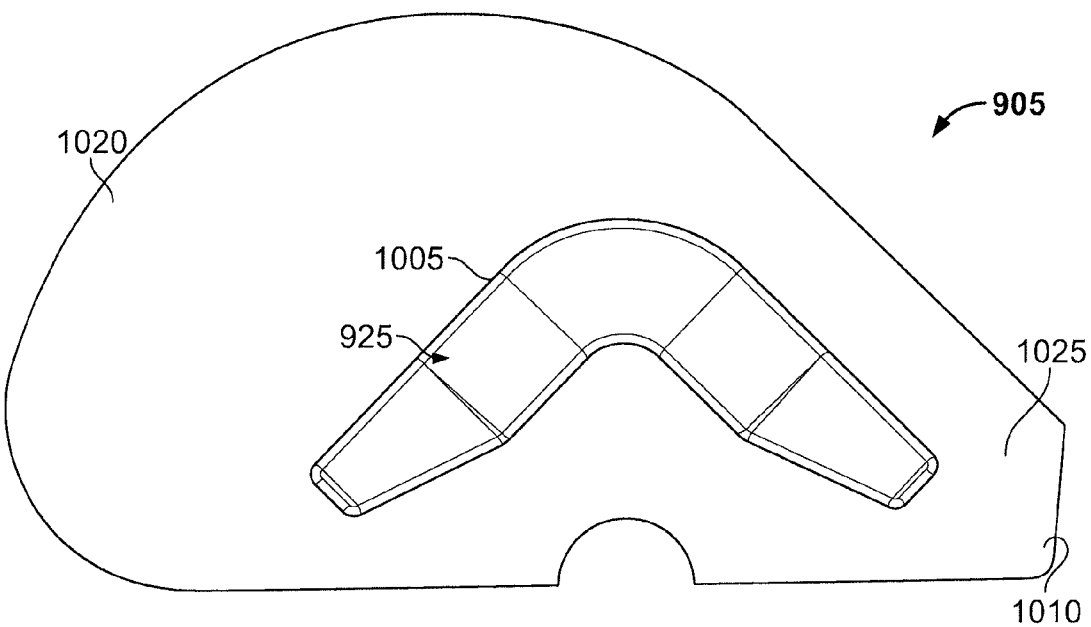
FIG. 10 shows a top, plan view of an exemplary embodiment of a blister member of the drug container.
Figure 11:
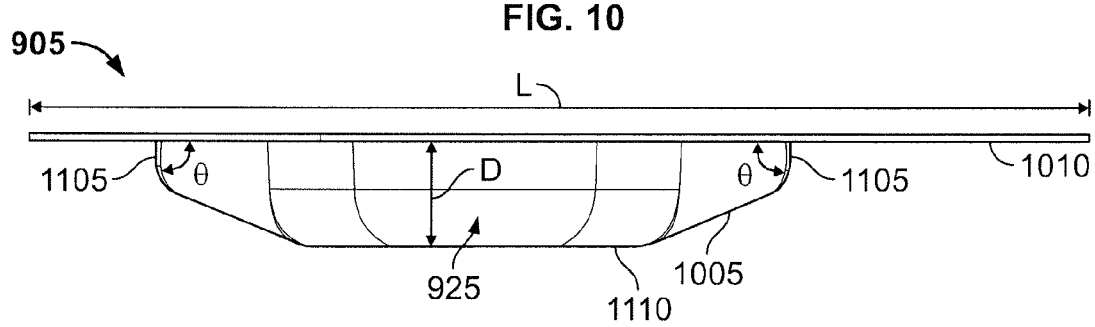
FIG. 11 shows a side, plan view of the blister member.
Figure 12:
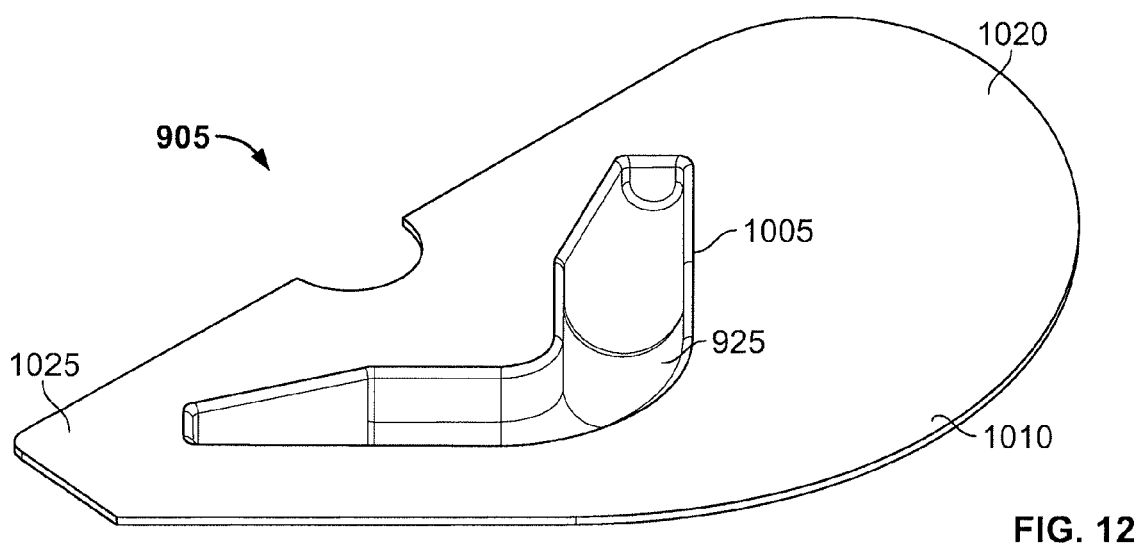
FIG. 12 shows a perspective, top view of the blister member.

The drug container 115 includes a guide member 930 that interacts with the inhaler 110 to assist in properly guiding the drug container 115 into a proper docked position during insertion of the drug container into the inhaler 110. In an embodiment, the guide member 930 is a cut-out having a shape that mates with a correspondingly-shaped protrusion in the inhaler 110 when the drug container 115 is properly docked into the inhaler 110. The cut-out is semicircular in the illustrated embodiment although the cut-out can have various shapes. The drug container 115 contains holes for the entrainment and exit of air. In FIG. 9 these are represented by an inlet hole 1410b and exit hole 1410a FIG. 10 shows a top, plan view of an exemplary embodiment of the blister member 905 of the drug container 115. FIG. 11 shows a side, plan view of the blister member 905. FIG. 12 shows a perspective, top view of the blister member 905. With reference to FIGS. 10-12, the blister member 905 includes a blister 1005 attached to a base 1010. The base 1010 is a generally flat or planar piece of material having a length L. The blister 905 is formed of one or more walls that extend outwardly from the base 1010 to define the drug chamber 925 for containment of the drug 920.

As shown in FIGS. 10 and 12, the base 1010 has a first, grasping region 1020 that can be sized and shaped to facilitate grasping of the drug container 115 by a user such as with the user's thumb and forefinger. In one embodiment, the grasping region 1020 has a planar size of approximately 0.275 square inches The peripheral edge of the grasping region 1020 can be rounded or widened to facilitate the user grasping onto the drug container. An insertion region 1025 is opposite the grasping region 1020. The insertion region 1025 is sized and shaped for insertion into the interface 415 of the mouthpiece 205 (FIGS. 4A and 4B). In this regard, the insertion region 1025 tapers in size moving away from the grasping region 1020.

As mentioned, the blister 1005 contains the drug 920. The blister 1005 has a shape that is adapted to facilitate transfer of the drug 920 from the blister 1005 and into the inhaler 110 during use. As shown in the side view of FIG. 11, the blister 1005 has side walls 1105 that extend outwardly from the base 1010 at an angle Θ. In one embodiment, the angle Θ is approximately 90 degrees relative to the base and in another embodiment the angle Θ is less than 90 degrees. In an embodiment, the angle Θ is at least a few degrees less than 90 degrees to allow removal of the blister from the mold during manufacture of the drug container. The angle Θ can be as close to 90 degrees as possible, because the more acute the angle is, the more tendency there is for powder to be trapped within the blister.

The side walls 1105 transition toward a roof or top wall 1110 that is spaced a distance D from the base 1010. The distance D can vary. In an embodiment, the distance D is in the range of 0.020 inch to 0.400 inch. The distance D can also vary at different locations of the blister. For example, in an embodiment, the distance D gradually lessens such that the top wall moves toward the base 1010 moving toward the outer tips of the lateral sections of the blister, as described below.

In an embodiment, the blister 1005 is formed of a transparent material that permits a user to view the drug contained in the blister. As described below, this permits the user to monitor the progress of drug transfer during inhalation and also permits the user to verify that all of the drug has been inhaled.

Figure 13:
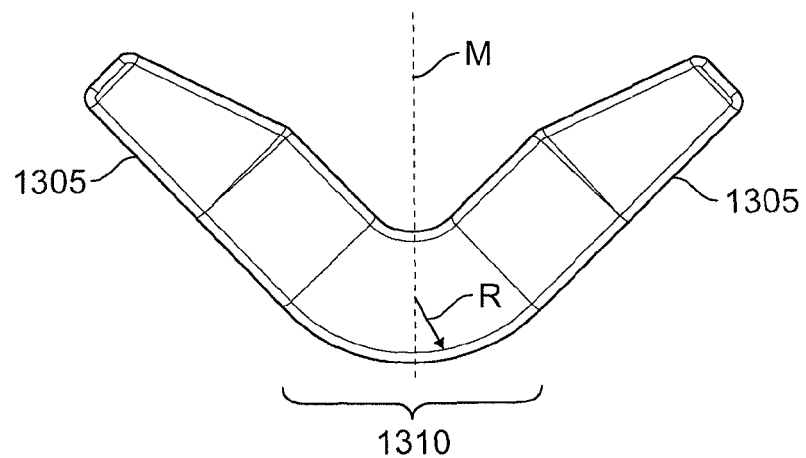
FIG. 13 shows a plan view of a blister of the blister member.

FIG. 13 shows a plan view of the blister 1005. In an embodiment, the blister has a pair of elongated lateral sections 1305 that extend outwardly from a vertex 1310 to provide the blister 1005 with a general "V" shape. The V shape can facilitate placement of the powdered drug in a single location in the blister. That is, the powdered drug tends to concentrate by gravity at the location of the vertex 310 where the drug can be more easily viewed than if the drug were spread out through the entire blister. In an embodiment, the volume of the vertex portion of the blister is such that there is empty space above the powdered drug when all of the powdered drug is positioned in the vertex. This allows for an initial airflow to begin sweeping the powder out of the blister.

In one embodiment, the vertex 1310 is rounded or curved along a radius of curvature R. The radius of curvature R can be constant along the vertex or it can vary. Moreover, the radius of curvature R can be selected in relation to the size of the particles of powder for the particular drug that is contained in the blister 1005. In an embodiment, the radius of curvature is approximately 0.200 inch. In another embodiment, the vertex 1310 is pointed rather than rounded such that the vertex is formed by straight rather than curved walls.

With reference still to FIG. 13, the lateral sections 1305 can extend outwardly from the vertex 1310 at various angles relative to a midline M. The lateral sections can be of identical shape and/or size relative to one another such that the blister has a shape that is a mirror image on either side of the midline M. Alternately, the lateral sections 1305 can have different sizes, shapes, and orientations relative to one another. The lateral sections 1305 can also have different cross-sectional shapes and sizes relative to the vertex 1305. In an embodiment, the cross-sectional area of the blister at the vertex 1305 is less than the cross-sectional area the lateral sections 1305 which can increase airspeed at the vertex and facilitate aspiration of the drug.

The angle between each of the lateral sections 1305 relative to the midline M may be varied to allow for different insertion configurations into the inhaler. In an embodiment, the vertex 1310 point substantially toward the ground during insertion so that gravity may concentrate the powder drug in the vertex 1310. In such an embodiment, any powder drug located in the extreme ends of the lateral sections 1305 slides down the lateral sections 1305 into the vertex 1310. To facilitate such sliding, at least a portion of the drug container can be made of a smooth, low friction material. The angle between the lateral section 1305 and the horizon can be up to 90 degrees to facilitate sliding. In one embodiment, the angle of each lateral section 1305 of the blister with the horizon is at least 45 degrees or greater.

It should be appreciated that the lateral sections 1305 are not necessarily symmetrically arranged relative to the midline M. For example, one of the lateral sections 1305 can be at a zero degree angle relative to the midline M, that is, vertical, while the opposite lateral section is at an angle of more than zero degrees, such as 45 degrees. This would facilitate the air entrance hole 1410b remaining outside the inhaler when the drug container is docked. In another embodiment, one of the lateral sections is shorter than the other lateral section such that even when the drug container is docked, the air entrance hole 1410b remains outside the inhaler. The blister can also have a composite shape, with the inferior portion of the lateral sections being in a "V" shape, and the ends of the lateral sections being parallel (arranged at 90 degrees) relative to the midline M. Various configurations are possible in order to accommodate a variety of blister insertion schemes.

Figure 14:
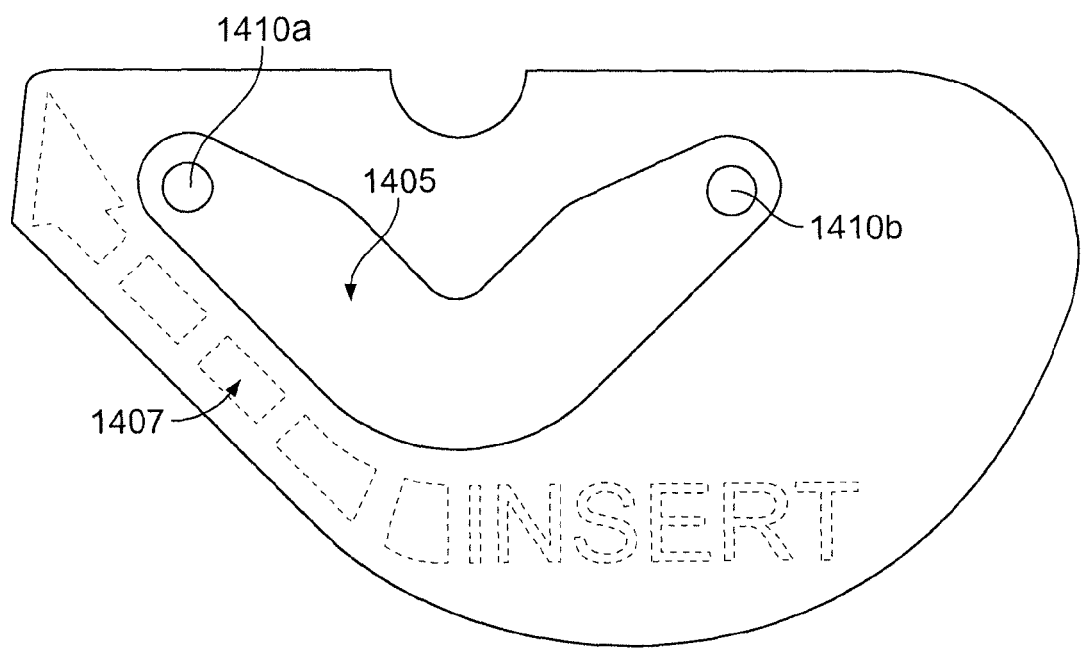
FIG. 14 shows a top view of a blister lid.

FIG. 14 shows a top view of the blister lid 910, which is a generally flat or planar member that is juxtaposed with the blister member 905 in the assembled drug container 115. The blister lid 910 encloses the blister 1005 to keep the drug within the drug chamber 920 of the blister 1005. The blister lid 905 has a size and shape that corresponds to the size and shape of the base 1010 of the blister member 905. The blister lid 905 includes a region 1405 that corresponds in size, shape, and position to the size, shape, and position of the blister 1005 on the blister member 905. The region 1405 can be of a different material or have a different quality than the remainder of the blister lid 910 to distinguish or highlight the blister 1005. For example, the region 1405 can be transparent such that the drug inside the blister 1005 can be viewed through the blister lid 910. A bottom side of the blister lid 910 can have adhesive for securing the blister lid 910 to the blister member 905.

The blister lid 1405 can include one or more symbols 1407 such as alphanumeric characters or other symbols that provide information regarding the use of the drug container 105. For example, as shown in the illustrated embodiment, the blister lid 1405 can include the words "INSERT" and an arrow that indicated which direction the drug container 115 is inserted into the inhaler 110.

With reference still to FIG. 14, at least two airflow ports comprised of holes 1410a and 1410b are located in the blister lid 905. As the patient inhales, air flows into the hole 1410b through the blister 1005 and out of the other hole 1410a. The holes 1410 are positioned to facilitate airflow through the entire blister such that all of the drug in the blister is exposed to the airflow. For example, in an embodiment, the hole 1410a is positioned at the tip of one of the lateral sections and the hole 1410b is positioned at the tip of the other lateral section. In addition, the hole 1410b is positioned outside of the inhaler 110 when docked in the inhaler 110, while the hole 1410a aligns with the airflow port 815 of the drug container interface 310 (FIGS. 6 and 8), as described in further detail below.

FIG. 14 only shows two holes 1410a and 1410b. However, more than two holes can be used. The holes in the blister may be varied in size, number and location to achieve a desired airflow profile. The holes can be configured to achieve a minimum level of airflow to disaggregate the powder. For example, if a rather high total inhaler airflow is needed to disaggregate a powder, the holes can be made smaller so that the patient has to inhale harder to empty the blister, thereby achieving a higher airflow through port 425, and subsequent higher flow through the disaggregation chamber 620. In this manner the patient can be assured that they have used the inhaler properly. If no drug remains in the blister, they know they have achieved a high enough airflow to properly aerosolize the powder. If drug remains in the blister, they may then increase their efforts on subsequent attempts, or be coached to do so, until they can use the inhaler properly. If they are still unable to empty the blister, they and their care giver then know that this particular drug/inhaler combination is not appropriate for them. In this manner, the inhaler gives great assurance as to proper use, and allows manufacturers to tailor the blister characteristics to their particular drug product.

In an exemplary embodiment, the holes 1410 are circular or rounded and have a diameter in the range of 0.040 inch to 0.080 inch. In an embodiment, at least one of the holes 1410a/1410b is replaced by two or more small holes that collectively provide a hole size that is substantially the same size as the single hole that was replaced. A single large hole can run a risk of the drug powder inadvertently falling out of the large hole. A plurality of small holes can function as a screen that keeps the drug powder from falling out of the blister. In an exemplary embodiment, the small holes each have a diameter that is no greater than about 0.050 inch. In an embodiment, the hole size is at least 0.010 inch and the maximum hole size is 0.080 inch. In another embodiment, at least some of the small holes have a diameter of about 0.020 inch. In an exemplary embodiment, there are no more than twenty small holes in place of one of the holes 1410 with each hole having a diameter of no greater than 0.020 inch. It should be appreciated that the foregoing hole sizes are exemplary and that the drug container can incorporate hole sizes different than the recited examples.

The blister lid 905 or the walls of the blister 1005 can include one or more aspiration holes that permit air to enter the blister but do not permit passage of the drug therethrough. In this regard, the aspiration holes can optionally have a maximum size that is less than the minimum size of the particles of drug powder. Thus, the aspiration holes can be sufficiently large to permit airflow into the blister but too small to permit the drug to pass through the aspiration holes. Alternately, the aspiration holes don't have to have a size smaller than the minimum particle size. Because powders typically have some cohesion, the aspiration holes can be larger than the particles and still prevent powder escape from the blister.

In an embodiment, the size of the blister 1005 tapers down in all dimensions to the size of the hole 1410 at the location of the hole or to the size of the collective area of multiple holes if multiple holes are present. Such a configuration avoids dead zones where there is no airflow. If dead zones are present, the drug powder tends to accumulate to inhibit the drug from flowing out of the drug container during inhalation. As mentioned, the blister 1005 defines an internal chamber 925 in which the drug 920 is contained. The chamber 925 has a volume that is greater than the total volume of drug contained in the blister 1005. This permits airflow to occur through the blister during use.

With reference again to FIG. 9, the removable lid 915 fits on top of the blister lid 915. The removable lid 915 serves to cover the holes 1410a and 1410b prior to use of the drug container 115. The removable lid 915 can be a foil-type of material with an adhesive on one side that permits the lid 915 to be removably positioned on top of the blister lid. The removable lid 915 can include symbols that provide instructions on use of the drug container with the inhaler.

The use of the drug transfer system 105 is now described. Immediately prior to use, the removable lid 915 is peeled off of the drug container 115 to expose the holes 1410a and 1410b. As mentioned, the holes 1410 communicate with the chamber 925 inside the blister 1005. The holes 1410 provide a means wherein air can flow into the blister 1005 to sweep the powdered drug out of the blister, into the inhaler 110, and into the patient's mouth during inhalation.

With the holes 1410 exposed as a result of removal of the removable lid 915, the drug container 115 is inserted into the inhaler 110. A user grasps the drug container 115 at the grasping region and inserts the insertion region of the drug container into the interface 415 of the mouthpiece 205. As mentioned, the drug container interface 310 (FIG. 5) is located inside the mouthpiece adjacent the interface 415 in the mouthpiece. The receptacle 810 of the drug container interface 310 is adapted to guide the insertion region of the drug container 115 into proper alignment with the inhaler 110. In this regard, the receptacle 810 has a shape that compliments the shape of the insertion region of the drug container 115 such that the drug container 115 moves into a predetermined orientation when inserted into the receptacle 810. For example, the receptacle 810 can have a wedge shape that compliments a similar wedge shape of the insertion region 1025 (shown in FIG. 10). Drug container 115 and receptacle 810 are constructed to provide enough friction or other holding mechanism to keep container 115 in place until forcibly removed.

Figure 15:
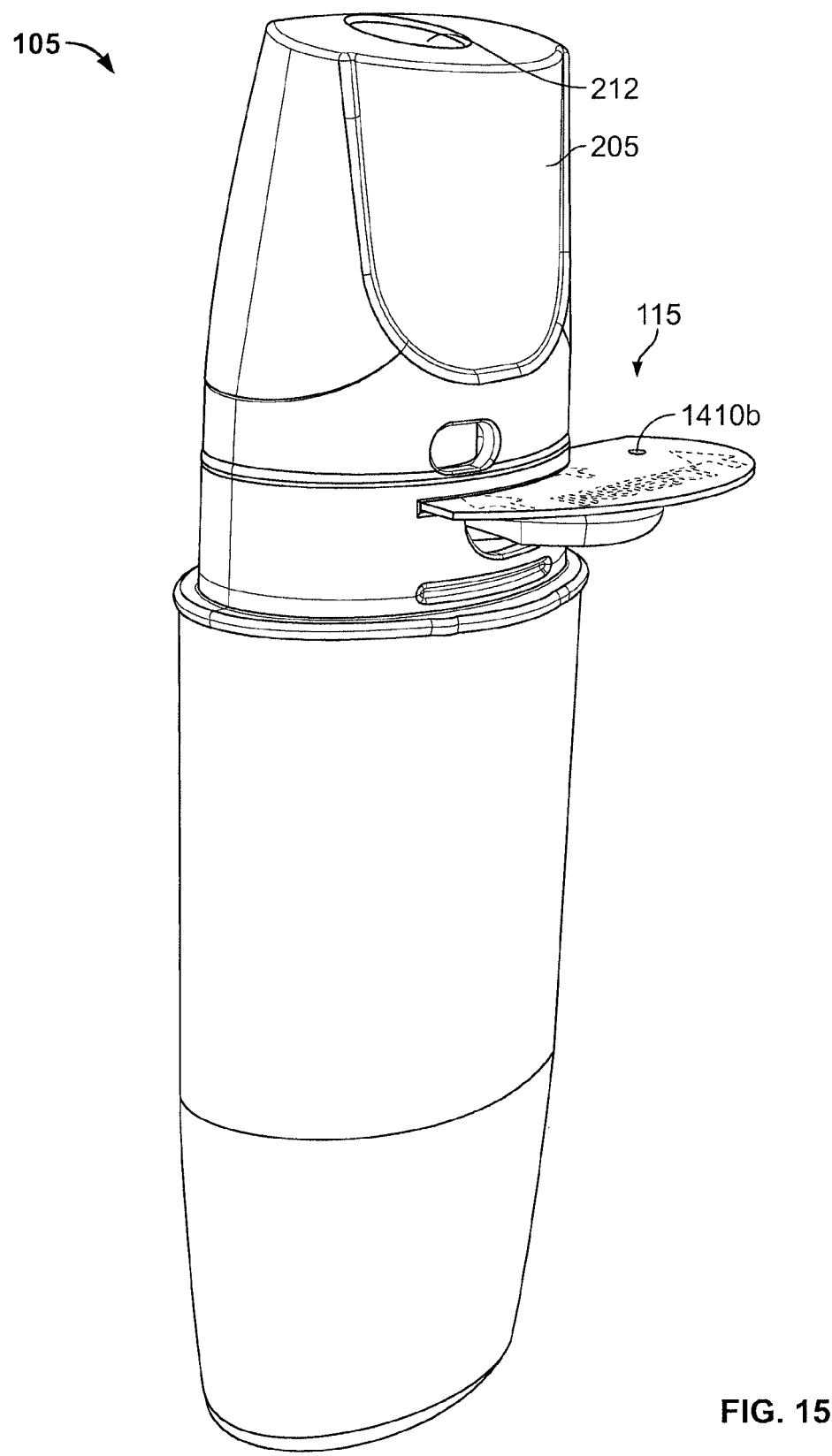
FIG. 15 shows the drug container docked into the inhaler.

FIG. 15 shows the drug container 115 docked into the inhaler 115. When properly docked, the hole 1410b is exposed and outside of the inhaler 115 while the hole 1410a is inside the inhaler. The hole 1410a aligns with the airflow port 815 of the drug container interface 310 (FIG. 6) inside the mouthpiece 205. As discussed, the airflow port 815 communicates with the entryway 510 of the disaggregation chamber 620. In this manner, the interior of the blister 1005 communicates with the disaggregation chamber 620 via the airflow port 815.

When in the properly docked state, the drug container 115 can be oriented such that the blister 1005 or a transparent region of the drug container is facing toward the user such that the user can view the blister 1005. As mentioned, the blister can be made of a transparent material that permits the user to see into the blister. This permits the user to monitor the progress of transfer of the drug from the blister into the inhaler as the user inhales. The blister 1005 could face forward (toward the user) or aft (away from the user). The blister 1005 or the blister lid 910, or both, could be entirely or partially transparent, such as depending on user defined functionality and/or possible manufacturing considerations. A transparent surface facing away from the user could enable real time inhalation monitoring by the user, using a mirror. Similarly, an aft facing transparent section allows a health professional or caregiver to monitor inhalation.

With the drug container 115 docked into the inhaler 110, the patient inserts the mouthpiece 205 into his mouth and inhales from the airflow port 212 of the mouthpiece 205. The airflow port 212 fluidly communicates with the interior of the blister 1005 via the internal chamber inside the mouthpiece 205 and the disaggregation chamber 620 of the airflow guide 305 inside the mouthpiece. The inhalation causes a pressure differential between the airflow port 212 and the interior of the blister 1005. The pressure differential causes air to flow into the blister 1005 through the hole 1410b. The air flows through the blister 1005 and out of the blister via the hole 1410a. As the air flows, the air sweeps the powdered drug out through the hole 1410a and through airflow port 815 into the entryway 510 of the disaggregation chamber 620.

The air along with the powdered drug flows through the disaggregation chamber 620. The spiral configuration of the disaggregation chamber 620 creates a turbulent airflow and abrasion against the chamber walls where the powdered drug disaggregates into an aerosol state The aerosol exits the disaggregation chamber 620 through the exit way 710 (FIG. 7) and enters the internal chamber of the mouthpiece 205. The aerosol then exits the mouthpiece 205 via the an airflow port 212 and enters into the patient's mouth. As mentioned, during or after inhalation of the drug, the user can observe the amount of drug remaining in the blister as the blister is made of a transparent material. Thus, the user can verify during or after inhalation that all of the drug has been inhaled during the process. This process facilitates coaching and adjustment of inspiratory effort during inhalation, or on subsequent inhalations, to train the user to use the proper inspiratory effort to empty the blister completely.

The inhaler 110 is adapted to have range of flow resistances in response to patient inhalation. The flow resistances are typically expressed as a pressure drop/flow/time such as in the units of centimeters of water(to 0.5 power)/Liters/minute. In one embodiment, the inhaler 110 provides a flow resistance range of approximately 0.020 to 0.400 (centimeter $H_2O^{0.5}$)/Liters/minute.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A drug dispenser package, comprising:
   a blister containing a powder formed of a plurality of particles, the blister including:
   (a) a vertex;
   (b) a first limb extending outwardly from the vertex, wherein an air entry port is positioned at an end of the first limb opposite the vertex, the air entry port providing an entryway for air to flow into the blister;
   (c) a second limb extending outwardly from the vertex, wherein an air exit port is positioned at an end of the second limb opposite the vertex, the air exit port providing an exitway for air to flow out of the blister with at least a portion of the powdered drug;
   an aspiration hole separate from the air entry port and air exit port, the aspiration hole having a size that is less than the minimum size of all the particles of the powder such that the aspiration hole is sufficiently large to permit airflow into the blister but too small to permit a particle of the powder to pass through the aspiration hole; and
   wherein the blister comprises side walls that extend outwardly from a base at an angle of 90 degrees relative to the base
   an inhaler that removably docks with the blister, the inhaler adapted to transfer drug from the blister into a patient upon inhalation of the patient from the inhaler, the inhaler including a mouthpiece that inserts into the patient's mouth, a cap removably attached to the mouthpiece and sized and shaped to provide a storage space for the blister, and a blister interface that is removably attached to the mouthpiece and the cap and adapted to receive the blister in a manner that positions the blister in the inhaler in a proper orientation for use, wherein the blister interface includes an airflow hole that aligns with the air exit port of the second limb when the blister is positioned in the blister interface.

2. A package as in claim 1, wherein the vertex has a radius of curvature.

3. A package as in claim 2, wherein the radius of curvature is approximately 0.200 inch.

4. A package as in claim 1, wherein at least one of the air entry port or air exit port is a single hole.

5. A package as in claim 4, wherein the single hole has a diameter in the range of 0.040 inch to 0.080 inch.

6. A package as in claim 1, wherein at least one of the air entry port or air exit port is a plurality of holes, each hole having a diameter of no more than about 0.050 inch.

7. A package as in claim 1, wherein at least one of the air entry port or air exit port is at least one hole having a diameter in the range of about 0.010 inch to about 0.080 inch.

8. A package as in claim 1, wherein at least one of the air entry port or air exit port is a plurality of small holes each having a diameter of about 0.020 inch.

9. A package as in claim 1, further comprising a guide member that interacts with an inhaler to assist in properly guiding the package into a proper docked position during insertion of the package into the inhaler, and wherein the guide member comprises a semicircular cut-out that extends into an edge of the blister.

10. A package as in claim 1, wherein the package generally includes a blister lid attached to the blister and a removable lid attached to the blister lid, the removable lid covering the air entry port and air exit port.

11. A package as in claim 1, wherein the blister is at least partially transparent.

12. A package as in claim 1, wherein the blister has a top wall and a base, the top wall spaced a distance of about 0.020 inch to about 0.400 inch from the base.

13. A package as in claim 12, wherein the distance between the top wall and the base varies at different locations of the blister.

14. A package as in claim 1, wherein the limbs are symmetric relative to a midline that extends through the vertex.

15. A package as in claim 1, wherein the vertex is shaped to facilitate placement of the powdered drug in a single location in the blister.

16. A package as in claim 15, wherein the volume of the vertex of the blister is such that there is empty space above the powdered drug when all of the powdered drug is positioned in the vertex.

17. A package as in claim 1, wherein the cross-sectional area of the blister at the vertex is less than the cross-sectional area at the locations of the ports.

18. A package as in claim 1, wherein the blister tapers in size moving toward at least one of the air entry port and the air exit port.

19. A drug transfer system, comprising:
(1) a blister containing a powder formed of a plurality of particles, the blister including:
   (a) a vertex;
   (b) a first limb extending outwardly from the vertex, wherein an air entry port is positioned at an end of the first limb opposite the vertex, the first air entry port providing an entryway for air to flow into the blister;
   (c) a second limb extending outwardly from the vertex, wherein an air exit port is positioned at an end of the second limb opposite the vertex, the air exit port providing an exitway for air to flow out of the blister with at least a portion of the powdered drug;
   (d) an aspiration hole separate from the air entry port and air exit port, the aspiration hole having a size that is less than the minimum size of all the particles of the powder such that the aspiration hole is sufficiently large to permit airflow into the blister but too small to permit a particle of the powder to pass through the aspiration hole, and wherein the blister comprises side walls that extend outwardly from a base at an angle of 90 degrees relative to the base; and
(2) an inhaler that removably docks with the blister, the inhaler adapted to transfer drug from the blister into a patient upon inhalation of the patient from the inhaler, the inhaler adapted to transfer drug from the blister into a patient upon inhalation of the patient from the inhaler, the inhaler including a mouthpiece that inserts into the patient's mouth, a cap removably attached to the mouthpiece and sized and shaped to provide a storage space for the blister, and a blister interface that is removably attached to the mouthpiece and the cap and adapted to receive the blister in a manner that positions the blister in the inhaler in a proper orientation for use, wherein the blister interface includes an airflow hole that aligns with the air exit port of the second limb when the blister is positioned in the blister interface.

20. A drug transfer system as in claim 19, wherein the inhaler includes a spiral disaggregation chamber.

21. A drug transfer system as in claim 19, wherein the blister has blister guide member having a shape that mates with a correspondingly-shaped inhaler guide member in the inhaler when the blister is properly docked into the inhaler.

22. A drug transfer system as in claim 19, wherein the blister guide member is a cut-out and the inhaler guide member is a protrusion.

23. A drug transfer system as in claim 19, wherein gravity concentrates drug in the vertex of the blister when the blister is docked in the inhaler.

24. A drug transfer system as in claim 19, wherein the air entry port is positioned outside of the inhaler and the air exit port is positioned inside the inhaler when the blister is docked in the inhaler.

25. A drug transfer system as in claim 19, wherein the inhaler has a flow resistance in response to patient inhalation, the flow resistance being in the range of about approximately 0.020 to approximately 0.400 (centimeter $H_2O^{0.5}$)/Liter/minute.

26. A drug transfer system as in claim 1 or 19, wherein at least one of the first limb and second limb is oriented relative to the vertex at an angle that is sufficiently steep to induce powder within the limb to slide into the vertex by the force of gravity.

* * * * *